United States Patent [19]

Morton et al.

[11] Patent Number: 5,023,074
[45] Date of Patent: Jun. 11, 1991

[54] STABILIZED AMINE FLUORIDE DENTAL CREAM

[75] Inventors: Anthony J. Morton, Ashton-uner-Lyne; Ian W. Stewart, Widnes; Kenneth Harvey, Wilmslow, all of England

[73] Assignee: Colgate-Palmolive Company, N.J.

[21] Appl. No.: 520,169

[22] Filed: May 7, 1990

Related U.S. Application Data

[63] Continuation of Ser. No. 268,624, Nov. 7, 1988, abandoned, which is a continuation of Ser. No. 862,842, May 13, 1986, abandoned.

[51] Int. Cl.$^5$ .......................... A61K 7/16; A61K 7/18; A61K 7/22
[52] U.S. Cl. .......................... 424/52; 424/49; 424/54; 424/57; 424/58
[58] Field of Search .......................... 424/49, 52, 54, 57, 424/58

[56] References Cited

U.S. PATENT DOCUMENTS

| 3,885,029 | 5/1975 | Norfleet et al. | 424/57 |
| 3,904,747 | 9/1975 | Cordon et al. | 424/49 |
| 3,914,406 | 10/1975 | Yankell | 424/52 |
| 3,935,304 | 1/1976 | Januszewski et al. | 424/49 |
| 3,935,305 | 1/1976 | Delaney et al. | 424/49 |
| 3,937,321 | 2/1976 | Delaney et al. | 206/84 |
| 3,943,240 | 3/1976 | Delaney et al. | 424/49 |
| 4,011,310 | 3/1977 | Soldati et al. | 424/52 |
| 4,105,759 | 8/1978 | Schreiber et al. | 424/52 |
| 4,160,022 | 7/1979 | Delaney et al. | 424/52 |
| 4,487,757 | 12/1984 | Kiozpeoplou | 424/71 |
| 4,490,353 | 12/1984 | Crawford et al. | 424/49 |

FOREIGN PATENT DOCUMENTS

| 865272 | 4/1961 | United Kingdom . |
| 1021058 | 2/1966 | United Kingdom . |
| 2164255A | 3/1986 | United Kingdom . |

Primary Examiner—Ronald W. Griffin
Attorney, Agent, or Firm—Murray M. Grill; Robert L. Stone

[57] ABSTRACT

Dental cream effective in promoting oral hygiene containing an amine fluoride, insoluble alkali metal metaphosphate polishing material, an aqueous humectant phase including at least one of glycerine and sorbitol and a solid phase containing non-ionic cellulosic gelling agent, wherein polyethylene glycol of average molecular weight of about 200–1000 is present to stabilize the dental cream against phase separation.

6 Claims, No Drawings

STABILIZED AMINE FLUORIDE DENTAL CREAM

This application is a Continuation of application Ser. No. 268,624, filed Nov. 7, 1988, now abandoned, which is a continuation of application Ser. No. 862,842, filed May 13, 1986, now abandoned.

This invention relates to a stabilized dental cream containing amine fluoride. In particular, it relates to a dental cream containing amine fluoride which is stabilized against phase separation by the presence of low molecular weight polyethylene glycol.

Amine fluoride compounds have been proposed and used in dental creams and other types of oral compositions, such as mouthwashes, for their effect in promoting oral hygiene. For instance, they have the ability to increase resistance of dental enamel to acids, thereby improving the ability of teeth to resist formation of cavities. They also can reduce formation of gingivitis and plaque in the oral cavity.

British Pat. Nos. 865,272 and 1,021,058, each to Gaba A. G. describe oral compositions including toothpastes and dental creams which contain amine fluoride compounds. In particular, in British Pat. No. 1,021,058, amine fluoride dental cream compositions are specifically exemplified wherein insoluble sodium metaphosphate is used as polishing agent, sorbitol is present as humectant and gelling agent, including methyl cellulose is also present. The patent also discusses glycerol (that is, glycerine) as an alternative humectant.

U.S. Pat. No. 3,914,406 to Yankell also describes amine fluoride oral compositions including toothpastes and includes an example wherein insoluble sodium metaphosphate polishing agent, sorbitol humectant and hydroxyethyl cellulose gelling agent are employed. The patent also discloses as humectants, "sorbitol, glycerine, polyhydric alcohols of like nature or mixtures thereof." However, in the specific examples the only mixtures (sorbitol solution and glycerine) are used in mouthwashes, while the toothpastes contain either sorbitol solution or propylene glycol.

It has been observed that dental creams such as are generally characteristic of the prior art undergo phase separation when the polishing agent has a substantial content of insoluble alkali metal metaphosphate, the humectant is sorbitol or glycerine and the gelling agent is non-polar cellulosic material. Use of alternative polyhydric alcohol of like nature as the sole or main humectant, for instance in amounts of about 15% or more, has not been satisfactory. For instance, when an amine fluoride dental cream containing 20% of polyethylene glycol of average molecular weight of about 600 is employed, an undesirable flavor note is provided.

It is an advantage of this invention that separation in amine fluoride dental cream of a liquid phase from the solid or gelled portion of the dental cream is reduced or overcome. Further advantages of the invention will be apparent from consideration of the following disclosures.

In accordance with certain of its aspects this invention relates to a dental cream comprising a material which provides to said dental cream about 0.01-1% by weight of soluble fluoride, at least about 70% by weight of said material being an amine fluoride, about 25-80% of an aqueous liquid phase comprising humectant in amount of at least about 20% by weight of said dental cream, said humectant selected from the group consisting of sorbitol, glycerine and mixture thereof, a solid phase comprising about 0.2-5% by weight of a non-ionic celluslosic gelling agent and about 20-75% by weight of a polishing material containing insoluble alkali metal metaphosphate as at least the major components of said polishing material, wherein said dental cream is stabilised against phase separation by incorporation into said aqueous humectant phase of polyethylene glycol having an average molecular weight of about 200–1000, wherein the weight ratio of said humectant to said polyethylene glycol is from about 10:1 to about 1:2, the amount of polyethylene glycol being at least about 2% by weight.

The term amine fluoride as used herein, includes amine hydrofluorides as well as quaternary ammonium fluorides. These are employed in amounts which provide about 0.01-1% by weight of soluble fluoride to the dental cream, preferably about 0.05-0.15%

Typically, they are characterized as having the formula:

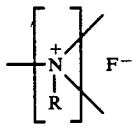

Wherein R represents alkyl, alkenyl, alkylol, alkoxyalkyl, aryl, aryloxyalkyl, aralkyl, cycloalkyl, cycloalkenyl or heterocyclic or an additional quaternary ammonium which may be attached to the nitrogen atom by a bridging group or a group of the formula $-R_1-CO.Y$ wherein Y represents OH, alkoxy, cycloalkoxy, aralkoxy or

where $R_1$ is alkylene or arylene-alkylene and each of $R_2$ and $R_3$ represents hydrogen or an alkyl, alkenyl, alkylol, aryl, aralkyl, cycloalkyl or heterocyclic radical, or $R_2$ and $R_3$ form together with the nitrogen atom a heterocyclic nucleus, each one of the three free valences being satisfied by alkyl, alkenyl, alkylol, alkoxyalkyl, aryl, aryloxyalkyl, aralkyl, cycloalkyl, or heterocyclic or at least two of the free valences being satisfied by a group forming together with the nitrogen atom, a saturated or unsaturated, unsubsituted or substituted heterocyclic nucleus.

The following compounds are specific examples of amine fluorides employed in accordance with this invention. The invention is not intended to be limited to these compounds.

Octyl-trimethyl-ammonium fluoride, dodecyl-ethyl-dimethyl-ammonium fluoride, tetraethyl ammonium flouride dilauryl-dimethyl-ammonium fluoride, Δ8,9 octadecenyl-benzyl-dimethyl-ammonium fluoride, furfuryl-lauryl-dimethyl-ammonium fluoride, phenoxyethyl-cetyl-dimethyl-ammonium fluoride, N,N,N',N'-tetramethyl-N,N'-dilauryl-ethylene-diammonium difluoride, N-cetyl-pyridinium fluoride, N,N-dilauryl-morpholinium fluoride, N-mytistyl-N-ethyl-morpholinium fluoride, N(octylamino-carbonylethyl)-N-benzyl-dimethyl-ammonium fluoride, N-2ethoxy-ethyl)-N-dodecyl-dimethyl-ammonium fluoride, N-(ω-hydroxydodecyl)-trimethyl-ammonium fluoride, N-(2-carbomethoxy-ethyl)-N-benzyl-dimethyl-ammonium fluoride, N-(2-carbo-cyclohexoxy-ethyl)-N myristyl-dimethyl-ammonium fluoride, N-(2-carbobenzyloxyethyl)-N-dodecyl-dimethyl-ammonium fluoride, N-(2-(N',N'-dimethylamino-carbonyl)-ethyl)-N-dodecyl-dimethyl-ammonium fluoride, and N-carboxymethyl-N-eicosyl-dimethyl-ammonium fluoride.

The amine fluorides of the present invention are soluble in water, and most of them are also soluble in methanol and ethanol. There are mostly hygroscopic crystalline solids or syrups. Those of the quaternary ammonium fluorides which have long-chain substituents dissolve in water with formation of foaming solutions.

Additional amine fluoride compounds which may be used in the present invention, and indeed are preferred, are amine hydrofluorides, having the formula:

RXHF

Wherein R represents alkyl or alkenyl groups having from about 10 to about 24 carbon atoms, advantageously from 14 to 21 carbon atoms;

X respresents $NH_2$ or

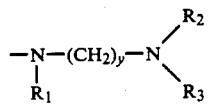

in which y is an integer of from 1 to 3, and $R_1$, $R_2$ and $R_3$ represents hydrogen; lower alkyl, lower alkenyl or lower alkanol having up to 5 carbon atoms.

Exemplary of compositions of this invention are those which comprise the hydrofluoride salts of decylamine, dodecylamine, dodecenylamine, tetradecylamine, tetradecenylamine, pentadecylamine, hexadecylamine, hexadecenylamine, octadecylamine, octadecenylamine, eicosylamine, tetracosylamine, and N-(bis-(hydroxethyl)-aminopropyl)-N-(hydroxyethyl) alkylamine wherein the alkylamine is a mixture of alkylamine groups containing from about 12 to about 18 carbon atoms.

Advantageous compositions of this invention are those which comprise 9-octadecenylamine hydrofluoride, hexadecylamine hydrofluoride, N-(Bis-(hydroxyethyl)-aminopropyl)-N(hydroxyethyl) octadecylamine dihydrofluoride, or N,N,N-Tris-(2-hydroxyethyl)-N-octadecyl-1,3-diamino-propane dihydrofluoride.

Further, a mixture of N-(Bis-(hydroxyethyl)-aminopropyl)-N-(hydroxyethyl) octadecylamine dihydrofluoride and hexadecylamine hydrofluoride is also desirable.

In accordance with preferred aspects of the invention, the entire soluble fluoride providing material is the amine fluoride. Also included is up to 30% by weight of the soluble fluoride providing material may be an additional non-toxic, water-soluble fluoride-providing compound or mixture thereof. Among these additional compounds (including mixtures thereof) are inorganic salts which provide fluoride, such as suitable alkali metal, alkaline earth metal, and heavy metal salts, for examples, sodium fluoride, potassium fluoride, ammonium fluoride, a copper fluoride, such as cuprous fluoride, zinc fluoride, a tin fluoride such as stannous fluoride or stannous chlorofluoride, sodium fluorosilicate, ammonium fluorosilicate, sodium fluorosilicate, ammonium fluorosilicate, sodium fluorozirconate, sodium monofluorophosphate, aluminum mono and difluorophosphate, and fluorinated sodium calcium pyrophosphate. When present, alkali metal salts such as sodium fluoride and sodium monofluorophosphate are preferred.

In dental cream formulations the liquids and solids are proportioned to form a creamy mass of desired consistency which is extrudable from a collapsible tube (for example, lacquered aluminium, wax-lined lead or laminated plastic) or a mechanically operated or pressure differential dispenser. The liquid phase comprises about 25-80% by weight of the dental cream and includes water together with at least one of sorbitol and glycerine as humectant, the amount of sorbitol and/or glycerine being at least about 20% by weight of the dental cream, preferably about 20-40%. Sorbitol is the preferred humectant and is typically employed as a 70% aqueous solution. Water is present, typically in amount of at least about 5% by weight, preferably about 15-40%.

The gelling agent for use in the dental cream formulations of the invention is a non-ionic cellulosic gelling agent, such as methyl cellulose, hydroxymethyl cellulose, ethyl cellulose, hydroxyethyl cellulose, propyl cellulose, hydroxypropyl cellulose and the like. Hydroxyethyl cellulose is preferred. The gelling agent is present in amount of about 0.2-5% by weight of the dental cream, preferably about 0.8-2.0%.

Grades of hydroxyethyl cellulose which may be used include the following:

| SUPPLIER | HEC GRADE | VISCOSITY (CPS) |
|---|---|---|
| Hercules | Natrosol 250M and MR | 4500-6500 |
| " | Natrosol 250 HR* and 250 H* | 1500-2500 |
| " | Natrosol 250 HHR* and 250 HH | 3400-5000 |
| B.P. Chemicals | Cellobond 5000 A | 4200-5600 |
| " | Cellobond 7000 A | 6000-7000 |
| Hoechst | Tylose H 4000 P** | 3000-5000 |
| " | Tylose H 10000 P** | 7000-12000 |

*1% solution (Brookfield; 25° C.)
**Hoeppler Viscometer (2%; 20° C.)

Natrosol 250 M is preferred.

The polishing material employed in the dental cream formulations is present in amounts of about 20-75% by weight, preferably about 35-65%. Most preferably it is all or substantially all insoluble alkali metal metaphosphate. It is within the scope of the present invention that insoluble alkali metal metaphosphate may be present as the major polishing agent (at least 50.0%) in admixture with a minor amount of secondary polishing agent, such as calcined alumina, dicalcium phosphate (anhydrous or dihydrate), calcium pyrophosphate, tricalcium phosphate, calcium carbonate, trimagnesium phosphate trihydrate and magnesium carbonate. When secondary polishing agent is present, it is preferred that it be in amount of up to about one-third the amount of insoluble alkali metal metaphosphate, with the weight ratio of insoluble alkali metal metaphosphate to secondary polishing agent being about 3:1 to about 99:1, preferably about 8:1 to about 12:1.

Insoluble sodium metaphosphate is the preferred salt of the water-insoluble alkali metal polymetaphosphates. It is known, for example, as Maddrell or Kurrol salt. Water-soluble polymetaphosphates such as di-, tri-, tetra-, or hexa-metaphosphate are not intended to be covered by the invention. These latter may, however, be present as impurities in the water-insoluble polymetaphosphates which can be used in accordance with the invention. The commercially available water-insoluble sodium polymetaphosphate may for example, contain up to 4% of a water-soluble metaphosphate.

Low molecular weight polyethylene glycol of average molecular weight of about 200-1000, preferably about 400-1000, disperses readily in the liquid vehicle and is effective to prevent the dental cream from undergoing phase separation or syneresis. In order to effect dispersion readily, grades of polyethylene glycol which are normally solid at room temperature are heated to liquify them. Low molecular weight polyethylene glycol is employed in amount such that the weight ratio of humectant (glycerine and/or sorbitol) to polyethylene glycol is from about 10:1 to about 1:2, preferably from about 2:1 to about 1:1. The polyethylene glycol is present in amount of at least about 2%, by weight, typically about 2-10% and preferably about 4-10%. Organic surface-active agents may be used in the dental cream of the present invention to achieve increased prophylactic action, assist in achieving thorough and complete dispersion of the instant compositions throughout the oral cavity, and render the dental creams more cosmetically acceptable. The organic surface-active material is typically non-ionic, ampholytic or cationic in nature, and it is preferred to employ as the surface-active agent a detersive material which imparts to the composition detersive properties.

Suitable surface-active materials include nonionic agents such as condensates of sorbitan monostearate with approximately 20 moles of ethylene oxide, condensates of ethylene oxide with propylene glycol ("Pluronic" materials) and amphoteric agents such as long chain (alkyl) amino-alkylene alkylated amine derivatives, which are available under the trademark "Miranol" such as Miranol C2M. Cationic surface-active germicides and antibacterial compounds such as di-isobutyl phenoxy ethoxy ethyl dimethyl benzyl ammonium chloride, benzyl dimethyl stearyl ammonium chloride, benzyl dimethyl stearyl ammonium chloride, tertiary amines having one fatty alkyl group (of from 12-18 carbon atoms) and two (poly) oxyethylene groups attached to the nitrogen (typically containing a total of from about 2 to 50 ethanoxy groups per molecule) and salts thereof with acids, and compounds of the structure

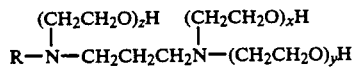

where R is a fatty alkyl group containing from about 12 to 18 carbon atoms, and x, y and z total 3 or higher, as well as salts thereof with mineral or organic acids, may also be used. It is preferred to use about 0.05-5% by weight of surface-active material.

Any suitable flavoring or sweetening materials may be employed in formulating a flavor for the composition of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methyl salicylate. Suitable sweetening agents include sucrose, lactose, maltose, xylitol, sodium 6-methyl-3, 4-dihydro-1,2,3-oxathiazine-4-one, sodium cyclamate, perillartine, sodium saccharin and saccharin acid. Suitably, flavor and sweetening agents may together comprise from about 0.01 to 5% or more of the compositions of the instant invention.

Various other materials may be incorporated in the dental cream. Examples thereof are coloring or whitening agents or dyestuffs, preservatives, anti-corrosive agents, silicones, chlorophylic compounds, additional ammoniated materials such as urea, diammonium phosphate and mixtures thereof and other constituents. Whitening agents, such as titanium dioxide, typically in amounts of about 0.05-2%, may be beneficial to the appearance of the dental composition, since upon aging, some discoloration may occur.

The adjuvants are incorporated in the instant compositions in amounts which do not substantially adversely affect the properties and characteristics desired and are selected and used in proper amounts depending upon the particular type of composition involved.

Antibacterial agents may also be employed in the oral compositions of the instant invention in an amount of about 0.01-5% by weight.

When an insoluble alkaline earth metal salt is present as the secondary polishing agent, there is typically employed various calcium and magnesium ion suppression agents for adjustment of physical properties of the compositions. Suitable agents are the water-soluble inorganic polyphosphate salts, such as tetrasodium pyrophosphate or disodium diacid pyrophosphate, with the partially neutralized or acid polyphosphate preferred. Other suitable agents are the alkali metal, preferably sodium, salts of citric acid. In general, such compounds will be a minor amount or proportion of the formulation. The precise amount will vary depending upon the specific formulation, such as the physical characteristics of the dental cream, but will usually be from about 0.1% to about 3% by weight.

The dental creams should have a pH practicable for use. A pH range of about 3.5 to 9 is particulary desirable. The reference to the pH is meant to be the pH determination directly on the dental cream. If desired, materials such as citric acid may be added to adjust to the pH to say preferably about 4-8.

The following illustrative examples are further illustrative of the nature of the present invention but it is understood that the invention is not limited thereto. All amounts and proportions are by weight except as otherwise indicated.

EXAMPLE 1

The following dental creams are prepared:

| | PARTS | |
|---|---|---|
| | A | B |
| Glycerine | 23.0 | 13.0 |
| Polyethylene Glycol 600 | — | 10.0 |
| Hydroxyethyl Cellulose (Natrosol 250M) | 1.5 | 1.5 |
| Sodium Saccharin | 0.4 | 0.4 |
| Water (Deionised) | 27.1 | 27.1 |
| Titanium Dioxide | 0.5 | 0.5 |
| Amine Fluoride* 33% | 4.0 | 4.0 |
| Insoluble Sodium Metaphosphate | 42.0 | 42.0 |
| Polyoxyethylene Sorbitan-Ethylene Oxide (20:1) Monostearate | 0.5 | 0.5 |
| Flavour | 1.1 | 1.1 |

*The Amine Fluoride is N,N,N'-tris (2-hydroxyethyl)-N'-octadecyl-1,3-diaminopropane dihydrofluoride.

N,N,N'-tris(2-hydroxyethyl)-N'-octadecyl-1,3-diaminopropane.

In preparing the above dental cream polyethylene glycol 600 is dispersed with glycerine prior to addition of hydroxyethyl cellulose to form a product of creamy consistency.

After aging for 12 weeks at 43° C., dental cream B remains substantially rheologically stable while substantial syneresis of dental cream A is observed with 4 weeks.

EXAMPLE 2

Dental creams C & D are prepared corresponding dental creams A and B respectively, except that sorbitol (70%) replaces glycerine.

After aging for 12 weeks at 43° C. only very slight phase separation is observed with dental cream D while substantial syneresis of dental cream C is observed within 12 weeks.

EXAMPLE 3

The amounts of glycerine and polyethylene glycol 600 in dental cream B are varied as follows:

| Dental Cream | Glycerine Parts | Polyethylene Glycol 600 Parts |
| --- | --- | --- |
| E | 20.0 | 2.0 |
| F | 19.0 | 3.0 |
| G | 18.0 | 4.0 |
| H | 16.0 | 6.0 |
| I | 14.0 | 8.0 |

After aging for 3 weeks at 49° C., only very slight phase separation is observed with dental cream E, only very slight phase separation with dental creams F and G after 9 weeks at 49° C. and substantially no phase separation is observed with dental creams H and I even after aging for 9 weeks at 49° C.

Polyethylene glycol of average molecular weights indicated below replaces polyethylene glycol 600 in dental cream B with the amounts of glycerine and polyethylene glycol also varied as indicated:

| Dental Cream | Glycerine Parts | Polyethylene Glycol Average Mol. wt. | Parts |
| --- | --- | --- | --- |
| J | 18.000 | 400 | 4.000 |
| K | 16.000 | 400 | 6.000 |
| L | 18.000 | 1000 | 4.000 |
| M | 16.000 | 1000 | 6.000 |

After aging for 9 weeks at 49° C. there is substantially no phase separation with dental creams J and L, only very very slight phase separation with dental cream K and only very slight phase separation with dental cream M. In dental creams J and L, glycerine is heated to 50° C. prior to dispersion of polyethylene glycol 1000 therein.

EXAMPLE 5

The amounts of sorbitol (70%) and polyethylene glycol 600 in dental cream D is varied as follows:

| Dental Cream | Sorbitol (70%) Parts | Polyethylene Glycol 600 Parts |
| --- | --- | --- |
| N | 18.000 | 4.000 |
| O | 17.000 | 5.000 |
| P | 16.000 | 6.000 |

After aging for 9 weeks at 49° C. there is substantially no phase separation with dental creams N and P and only an indication of very slight phase separation with dental cream O.

EXAMPLE 6

A dental cream which does not separate into phase upon aging is prepared by varying dental cream D to reduce the amount of insoluble sodium metaphosphate to 37.8 parts and including 4.2 parts of calcined alumina.

EXAMPLE 7

The following dental creams do not separate into phases upon aging.

| | Parts | |
| --- | --- | --- |
| | A | B |
| Glycerine | 16.000 | 16.000 |
| Polyethylene Glycol 600 | 6.000 | 6.000 |
| Hydroxyethyl cellulose (Natrosol 250M) | 1.500 | 1.500 |
| Sodium Saccharin | 0.400 | 0.400 |
| Water (Deionised) | 29.133 | 29.053 |
| Titanium Dioxide | 0.500 | 0.500 |
| Amine Fluoride *(33%) | 2.800 | 2.800 |
| Sodium Monoflurophosphate | — | 0.114 |
| Sodium Fluroide | 0.067 | 0.033 |
| Insoluble Sodium Metaphosphate | 42.000 | 42.000 |
| Polyoxyethylene Sorbitan-Ethylene Oxide (20:1) Monostearate | 0.500 | 0.500 |
| Flavour | 1.1 | 1.1 |

*The Amine Fluoride is N,N,N-tris (2-hydroxyethyl)-N-octadecyl-1,3-diaminopropane dihydrofluoride.

In the foregoing examples, the 4.0 parts of the 33% solution of the Amine Fluoride may be replaced by 4.344 parts of a 1:4 mixture of N-(Bis-(hydroxyethyl)-aminopropyl)-N-(hydroxyethyl) octadecylamine dihydrofluoride and hexadecylamine hydrofluoride, with similar results.

In the foregoing examples, sodium cyclamate may replace sodium saccharine.

It is apparent that the above examples illustrate the invention and various modifications may be made thereto.

We claim:

1. In a process for stabilizing a flavored dental cream against phase separation, which dental cream comprises a fluoride providing compound which provides to said dental cream about 0.01–1% by weight of soluble fluoride, at least about 70% by weight of said fluoride-providing compound being an amine fluoride selected from the group consisting of a quaternary ammonium fluoride and an amine hydrofluoride having the formula:

RXHF wherein R is alkyl or alkenyl containing about 10–24 carbon atoms, X is $NH_2$ or

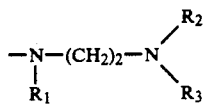

wherein y is an interger of 1-3 and $R_1$, and $R_3$ are hydrogen or lower alkyl, lower alkenyl or lower alkanol containing up to 5 carbon atoms, about 25-80% by weight of an aqueous liquid phase comprising humectant in amount of at least about 20% by weight of said dental cream, said humectant being selected from the group consisting of sorbitol, glycerine and mixture thereof, a solid phase comprising about 0.2-5% by weight of a non-ionic cellulosic gelling agent, about 0.01-5% by weight of flavor and sweetening agents and about 20-75% by weight of a polishing material containing insoluble alkali metal metaphosphate as at least the major component of said polishing material, the improvement wherein polyethylene glycol having an average molecular weight of about 200-1000 is incorporated into said aqueous liquid phase, wherein the weight ratio of said humectant to said polyethylene glycol is from about 10:1 to about 1:2 and the amount of polyethylene glycol is about 2%-10% by weight, which amount is less than 20% by weight, at which 20% amount, polyethylene glycol of average molecular weight of about 600 provides an undesirable flavor note, thereby stabiliaing said flavored dental cream against phase separation.

2. The process claimed in claim 1 wherein the weight ratio of said humectant to said polyethylene glycol is from about 10:1 to about 13:10.

3. The process claimed in claim 1 wherein said amine fluoride is N,N,-N'-tris(2-hydroxyethyl)-N'-octadecyl-1,3-diaminopropane.

4. The process claimed in claim 1 wherein said polyethylene glycol is present in amount of about 4-10%.

5. The process claimed in claim 4 wherein said polyethylene glycol has an average molecular weight of about 400-1000.

6. The process claimed in claim 5 wherein said polyethylene glycol has an average molecular weight of about 600.

* * * * *